(12) United States Patent
Romo et al.

(10) Patent No.: US 12,350,092 B2
(45) Date of Patent: Jul. 8, 2025

(54) SYSTEMS FOR A TRIPLE IMAGING HYBRID PROBE

(71) Applicant: Noah Medical Corporation, San Carlos, CA (US)

(72) Inventors: Enrique Romo, Danville, CA (US); Hendrik Thompson, San Francisco, CA (US); Lisa Heaton, Flagler Beach, FL (US)

(73) Assignee: NOAH MEDICAL CORPORATION, San Carlos, CA (US)

( * ) Notice: Subject to any disclaimer, the term of this patent is extended or adjusted under 35 U.S.C. 154(b) by 77 days.

(21) Appl. No.: 18/054,792

(22) Filed: Nov. 11, 2022

(65) Prior Publication Data

US 2023/0075251 A1 Mar. 9, 2023

Related U.S. Application Data

(63) Continuation of application No. PCT/US2021/034856, filed on May 28, 2021.

(Continued)

(51) Int. Cl.
*A61B 8/08* (2006.01)
*A61B 1/00* (2006.01)
(Continued)

(52) U.S. Cl.
CPC .......... *A61B 8/085* (2013.01); *A61B 1/00148* (2022.02); *A61B 1/0055* (2013.01);
(Continued)

(58) Field of Classification Search
CPC ....... A61B 8/085; A61B 8/0841; A61B 34/20; A61B 34/30; A61B 8/12; A61B 8/4254;
(Continued)

(56) References Cited

U.S. PATENT DOCUMENTS 6,338,717 B1 * 1/2002 Ouchi .................... A61B 8/445
600/464
9,220,400 B2 12/2015 Petersen
(Continued)

FOREIGN PATENT DOCUMENTS

WO WO-2010140441 A1 12/2010
WO WO-2021247418 A1 12/2021

OTHER PUBLICATIONS

PCT/US2021/034856 Search Report and Written Opinion dated Nov. 1, 2021.
(Continued)

*Primary Examiner* — Chao Sheng
(74) *Attorney, Agent, or Firm* — WILSON SONSINI GOODRICH & ROSATI

(57) ABSTRACT

A hybrid vision device is provided. The hybrid vision device comprises: an articulating elongate member comprising a proximal end and a distal end, and a positional sensor is located at the distal end of the articulating elongate member; and a multimodal sensing probe removably coupled to the articulating elongate member, and the multimodal sensing probe comprises an ultrasound transducer and a camera located at a distal portion of the multimodal sensing probe.

16 Claims, 11 Drawing Sheets

Related U.S. Application Data

(60) Provisional application No. 63/033,624, filed on Jun. 2, 2020.

(51) Int. Cl.
    *A61B 1/005*     (2006.01)
    *A61B 1/018*     (2006.01)
    *A61B 1/05*     (2006.01)
    *A61B 1/06*     (2006.01)
    *A61B 1/267*     (2006.01)
    *A61B 8/00*     (2006.01)
    *A61B 8/12*     (2006.01)
    *A61B 34/20*     (2016.01)
    *A61B 34/30*     (2016.01)

(52) U.S. Cl.
    CPC ............ *A61B 1/0057* (2013.01); *A61B 1/018* (2013.01); *A61B 1/053* (2013.01); *A61B 1/0676* (2013.01); *A61B 1/2676* (2013.01); *A61B 8/0841* (2013.01); *A61B 8/12* (2013.01); *A61B 8/4254* (2013.01); *A61B 8/4416* (2013.01); *A61B 8/445* (2013.01); *A61B 8/4488* (2013.01); *A61B 34/20* (2016.02); *A61B 34/30* (2016.02); *A61B 2034/2051* (2016.02); *A61B 2034/2063* (2016.02); *A61B 2034/301* (2016.02)

(58) Field of Classification Search
    CPC ..... A61B 8/4416; A61B 8/445; A61B 8/4488; A61B 2034/2051; A61B 2034/2063; A61B 2034/301; A61B 1/00148; A61B 1/0055; A61B 1/0057; A61B 1/018; A61B 1/053; A61B 1/0676; A61B 1/2676
See application file for complete search history.

(56) References Cited

U.S. PATENT DOCUMENTS

| | | | |
|---|---|---|---|
| 2006/0149129 A1* | 7/2006 | Watts ................... | A61B 1/0125 600/113 |
| 2007/0232898 A1* | 10/2007 | Huynh ................. | A61B 5/1076 600/587 |
| 2007/0239010 A1* | 10/2007 | Johnson .................... | A61B 8/12 600/439 |
| 2009/0062871 A1 | 3/2009 | Chin et al. | |
| 2011/0288561 A1* | 11/2011 | Devengenzo .......... | G16H 20/40 606/130 |
| 2014/0276108 A1 | 9/2014 | Vertikov | |
| 2019/0008490 A1 | 1/2019 | Greminger et al. | |
| 2019/0142528 A1 | 5/2019 | Vertikov | |
| 2019/0247127 A1 | 8/2019 | Kopel et al. | |
| 2019/0254649 A1 | 8/2019 | Walters et al. | |
| 2019/0282203 A1* | 9/2019 | Naumann ................ | A61B 8/00 |
| 2019/0298451 A1 | 10/2019 | Wong et al. | |

OTHER PUBLICATIONS

European Patent Application No. 21817212.0 Extended European Search Report dated May 17, 2024.
JP Serial No. 2022-570117 Office Action dated Mar. 12, 2025.

* cited by examiner

SYSTEMS FOR A TRIPLE IMAGING HYBRID PROBE

REFERENCE

This application is a Continuation Application of International Application No. PCT/US2021/034856, filed May 28, 2021, which claims the benefit of U.S. Provisional Application No. 63/033,624, filed Jun. 2, 2020, which applications are incorporated herein by reference.

BACKGROUND OF THE INVENTION

Early diagnosis of lung cancer is critical. The five-year survival rate of lung cancer is around 18% which is significantly lower than the next three most prevalent cancers: breast (90%), colorectal (65%), and prostate (99%). A total of 142,000 deaths were recorded in 2018 due to lung cancer.

When a patient has been diagnosed with a suspicious lung lesion, they may be referred to a physician to obtain a biopsy of the lesion to determine if it is malignant. If the tissue sample is determined to be malignant, an endobronchial treatment of the lung cancer may be performed. In a typical process, pre-operative imaging such as computed tomography (CT) may be performed to identify lesions of the patient's lungs. The CT images may be used to provide anatomical location information of the lesion such as to generate a map to guide the navigation of the bronchoscope at the time of bronchoscopy. During bronchoscopy, a bronchoscopy system equipped with sensors such as electromagnetic (EM) three-dimensional (3D) sensors may register itself to the CT image or the patient anatomy. The EM information along with a direct visualization system (e.g., camera) may allow the physician to manipulate the bronchoscope to the site of the lesion.

If the lesion resides at least partially within the airways that it is captured in the view of the direct visualization system, the physician may navigate the endoscope towards the lesion and proceed to acquire a tissue biopsy of the lesion. However, a challenge arises when the lesion is outside the airway where the lesion is outside of the view of the direct visualization system of the bronchoscope. In this scenario, the lesion is not visible to the physician in the camera view and the physician may have to rely on information from the EM sensor and the pre-operative image which does not provide accurate and real-time location of the lesion relative to the bronchoscope.

SUMMARY OF THE INVENTION

Recognized herein is a need for a minimally invasive system that allows for performing surgical procedures or diagnostic operations with improved visualization. The present disclosure provides systems and methods allowing for early lung cancer diagnosis and treatment with improved real-time visualization. In particular, the present disclosure provides a bronchoscopy device with multimodal hybrid vision. The bronchoscope may integrate electromagnetic (EM) sensor, direct imaging device, and ultrasound imaging allowing physicians to visualize tissue variations within the lung, specifically outside the airways. For example, incorporating an ultrasound probe into the bronchoscope may allow a physician to scan an area of interest and confirm the actual location of the lesion relative to the bronchoscope with improved accuracy. The provided bronchoscope may provide a hybrid vision capability by combining the use of the EM sensor, direct imaging sensor, and ultrasound sensor.

It should be noted that the provided endoscope systems can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

In an aspect of the disclosure, a hybrid vision device is provided. The hybrid vision device comprises: an articulating elongate member comprising a proximal end and a distal end, and a first positional sensor is located at the distal end of the articulating elongate member; and a multimodal sensing probe removably coupled to the articulating elongate member. The multimodal sensing probe comprises an ultrasound transducer and a camera located at a distal portion of the multimodal sensing probe.

In some embodiments, the multimodal sensing probe is inserted through a first lumen of the articulating elongate member. In some embodiments, the multimodal sensing probe is rotatable and extendible relative to the articulating elongate member. In some embodiments, the multimodal sensing probe is articulatable relative to the articulating elongate member.

In some embodiments, the multimodal sensing probe further comprises a second positional sensor located at the distal portion of the multimodal sensing probe to track a location of the distal portion of the multimodal sensing probe. In some cases, the second positional sensor, the camera and an illuminating device are embedded into the distal portion of the multimodal sensing probe. In some instances, the second positional sensor, the camera and the illuminating device are arranged in a compact configuration. In some cases, the articulating elongate member and the multimodal sensing probe are robotically controlled based at least in part on the sensor data captured by the first positional sensor and the second positional sensor.

In some embodiments, the ultrasound transducer is an array of linear endobronchial ultrasound (EBUS) transducers. In some embodiments, the camera provides a real-time forward view and the ultrasound transducer provides a real-time side view. In some cases, the articulating elongate member comprises a second lumen for receiving an instrument. In some instances, a movement of the instrument is captured by the real-time side view.

In some embodiments, the articulating elongate member further comprises an imaging device located at the distal end of the articulating elongate member. In some embodiments, the multimodal sensing probe comprises an inflatable tip to provide contact or to seal a passageway inside a body.

In another aspect, the disclosure provides a hybrid vision device comprising: an articulating elongate member comprising a distal tip portion and a bending section; an ultrasound transducer located at the distal tip portion to provide a side view; and a channel configured to receive an instrument, wherein the lumen has a port located at the bending section allowing the instrument to extend out of the port along a trajectory that intersects the side view or the ultrasound image.

In some embodiments, the articulating elongate member comprises a positional sensor located at the distal tip portion. In some instances, the positional sensor is embedded into the distal tip portion to track a location of the distal tip portion. In some embodiments, the articulating elongate member comprises a camera embedded into the distal tip portion. In some cases, the camera provides a real-time forward view.

In some embodiments, the ultrasound transducer is an array of linear endobronchial ultrasound (EBUS) transducers.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION OF THE INVENTION

Figure 1:
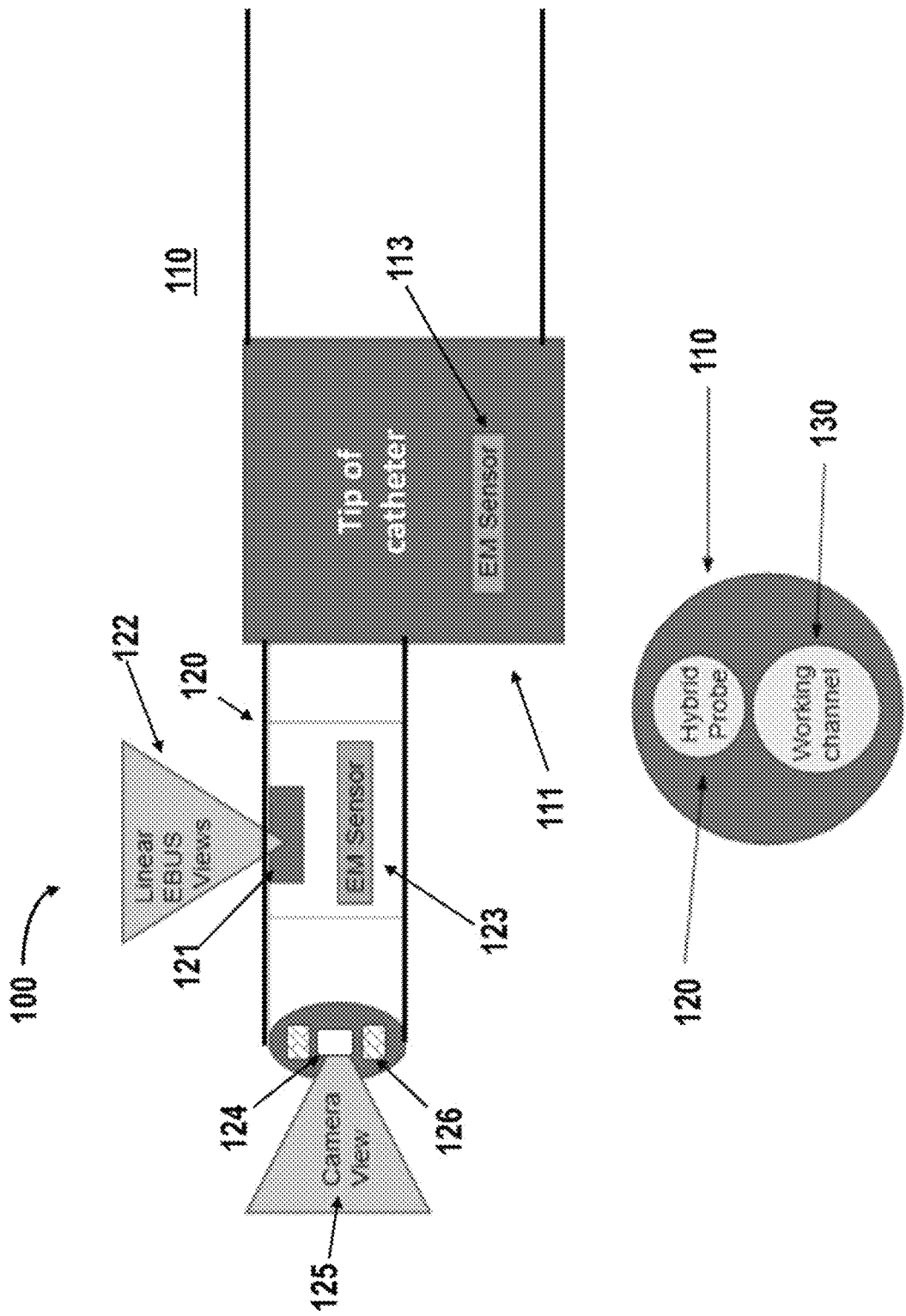
FIG. 1 shows an example of an assembly of an endoscope system, in accordance with some embodiments of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

While exemplary embodiments will be primarily directed at a bronchoscope, one of skill in the art will appreciate that this is not intended to be limiting, and the devices described herein may be used for other therapeutic or diagnostic procedures and in other anatomical regions of a patient's body such as a digestive system, including but not limited to the esophagus, liver, stomach, colon, urinary tract, or a respiratory system, including but not limited to the bronchus, the lung, and various others.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Although the treatment planning and definition of diagnosis or surgical procedures as described herein are presented in the context of pulmonary diagnosis or surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein a processor encompasses one or more processors, for example a single processor, or a plurality of processors of a distributed processing system for example. A controller or processor as described herein generally comprises a tangible medium to store instructions to implement steps of a process, and the processor may comprise one or more of a central processing unit, programmable array logic, gate array logic, or a field programmable gate array, for example. In some cases, the one or more processors may be a programmable processor (e.g., a central processing unit (CPU), graphic processing unit (GPU), or a microcontroller), digital signal processors (DSPs), a field programmable gate array (FPGA) and/or one or more Advanced RISC Machine (ARM) processors. In some cases, the one or more processors may be operatively coupled to a non-transitory computer readable medium. The non-transitory computer readable medium can store logic, code, and/or program instructions executable by the one or more processors unit for performing one or more steps. The non-transitory computer readable medium can include one or more memory units (e.g., removable media or external storage such as an SD card or random access memory (RAM)). One or more methods or operations disclosed herein can be implemented in hardware components or combinations of hardware and software such as, for example, ASICs, special purpose computers, or general purpose computers.

As used herein, the terms distal and proximal may generally refer to locations referenced from the apparatus, and can be opposite of anatomical references. For example, a distal location of a bronchoscope or catheter may correspond to a proximal location of an elongate member of the patient, and a proximal location of the bronchoscope or catheter may correspond to a distal location of the elongate member of the patient.

An endoscope system as described herein, includes an elongate portion or elongate member such as a catheter. The terms "elongate member" and "catheter" are used interchangeably throughout the specification unless contexts suggest otherwise. The elongate member can be placed directly into the body lumen or a body cavity. In some embodiments, the system may further include a support apparatus such as a robotic manipulator (e.g., robotic arm) to drive, support, position or control the movements and/or operation of the elongate member. Alternatively or in addition to, the support apparatus may be a hand-held device or other control devices that may or may not include a robotic system. In some embodiments, the system may further include peripheral devices and subsystems such as imaging systems that would assist and/or facilitate the navigation of the elongate member to the target site in the body of a subject.

The endoscope system of the present disclosure may combine multiple sensing modalities to provide enhanced vision capability. In some embodiments, the multimodal sensing system may comprise at least positional sensing (e.g., EM sensor system, optical shape sensor, accelerometers, gyroscopic sensors), direct vision (e.g., camera), and ultrasound imaging.

In some cases, the endoscope system may implement a positional sensing system such as electromagnetic (EM) sensor, fiber optic sensors, and/or other sensors to register and display a medical implement together with preoperatively recorded surgical images thereby locating a distal portion of the endoscope with respect to a patient body or global reference frame. The position sensor may be a component of an EM sensor system including one or more conductive coils that may be subjected to an externally generated electromagnetic field. Each coil of EM sensor system used to implement positional sensor system then produces an induced electrical signal having characteristics that depend on the position and orientation of the coil relative to the externally generated electromagnetic field. In some cases, an EM sensor system used to implement the positional sensing system may be configured and positioned to measure at least three degrees of freedom e.g., three position coordinates X, Y, Z. Alternatively or in addition to, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point.

The direct vision may be provided by an imaging device such as a camera. A camera may comprise imaging optics (e.g. lens elements), image sensor (e.g. CMOS or CCD), and illumination (e.g. LED or fiber-based light). The imaging device may be located at the distal tip of the catheter or elongate member of the endoscope. In some cases, the direct vision system may comprise an imaging device and an illumination device. In some embodiments, the imaging device may be a video camera. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor and circuitry to combine or serialize the data so that it can be transmitted in a minimum number of electrical conductors. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors. As described later herein, the imaging device may be located at the distal tip of the catheter, an independent hybrid probe which is assembled to the endoscope, or a combination of both.

The provided endoscope system may use ultrasound to help guide physicians to a location outside of an airway. For example, a user may use the ultrasound to locate, in real-time a lesion location to guide the endoscope to a location where a computed tomography (CT) scan (pre-operative imaging) revealed the approximate location of a solitary pulmonary nodule. In some embodiments, the ultrasound may be a linear endobronchial ultrasound (EBUS), also known as convex probe EBUS, which may image to the side of the endoscope device. For example, a linear endobronchial ultrasound (EBUS) transducer or transducer array may be located at the distal portion of the endoscope providing a view that is parallel to the shaft of the endoscope. In some cases, the ultrasound may be a radial probe EBUS which images radially 360°.

The multi-modal sensing system may beneficially improve the vision capability of the endoscope device. For instance, the EM sensor may provide GPS-like navigation information for a user to navigate to the target site and use the direct visualization camera to view the anatomical landmarks and features to further confirm location relative to the pre-operative image (e.g., CT scan 3D model). Once at the target site, if the lesion is not visible in the airway, the ultrasound information may be used to identify the accurate location of the lesion on-site and in real-time. The ultrasound imaging may be used to visualize a depth (e.g., several millimeters or centimeters) into tissue next to the ultrasound transducer, to ascertain the exact location of a lesion for the purpose of either taking a biopsy or delivering a treatment or therapy (e.g., pharmacologic, mechanical, thermal therapy). In some cases, the ultrasound position may be registered to the EM sensor-based 3D position information such that the lesion location identified by the ultrasound imaging may be used to automatically control the position of the tip of the catheter or an instrument location.

In some embodiments, an ultrasound probe may be removably incorporated into a bronchoscopy system to enhance the vision guidance to a user. The ultrasound probe may comprise an ultrasound transducer located at the distal portion of the probe and may be capable to move along the length of the endoscope.

In some embodiments, a hybrid probe may be assembled to an existing bronchoscope system. The hybrid probe may include at least a camera, a positional sensor (e.g., EM sensor) and ultrasound transducer to provide a multi-modal sensing capability to the endoscope assembly. The bronchoscope may be an articulating device which is controlled to navigate the pathway under the guidance provided by the hybrid probe. In other embodiments, the hybrid probe may include a positional sensor (e.g., EM sensor) and an ultrasound transducer while the articulating device may include the camera and a positional sensor (e.g., EM sensor).

FIG. 1 shows an example of an assembly of an endoscope system 100, in accordance with some preferred embodiments of the present disclosure. The endoscope system 100 may comprise an articulating bronchoscope 110 and a hybrid probe 120. The hybrid probe 120 may be removably assembled to the bronchoscope such as by inserting through a channel of the bronchoscope catheter.

The bronchoscope 110 may include suitable means for deflecting the distal tip 111 of the scope to follow the pathway of the structure under examination, with minimum deflection or friction force upon the surrounding tissue. For example, control cables or pulling cables are carried within the endoscope body in order to connect an articulation section adjacent to the distal end 111 to a set of control mechanisms at the proximal end of the endoscope (e.g., handle) or a robotic support system.

The robotic bronchoscope system 100 can be releasably coupled to an instrument driving mechanism. The instrument driving mechanism may be mounted to the arm of the robotic support system or to any actuated support system. The instrument driving mechanism may provide mechanical and electrical interface to the robotic bronchoscope system 100. The mechanical interface may allow the robotic bronchoscope system 100 to be releasably coupled to the instrument driving mechanism. For instance, the handle portion of the robotic bronchoscope 110 can be attached to the instrument driving mechanism via quick install/release means, such as magnets and spring-loaded levels. In some cases, the robotic bronchoscope 110 may be coupled to or released from the instrument driving mechanism manually without using a tool.

Figure 8:
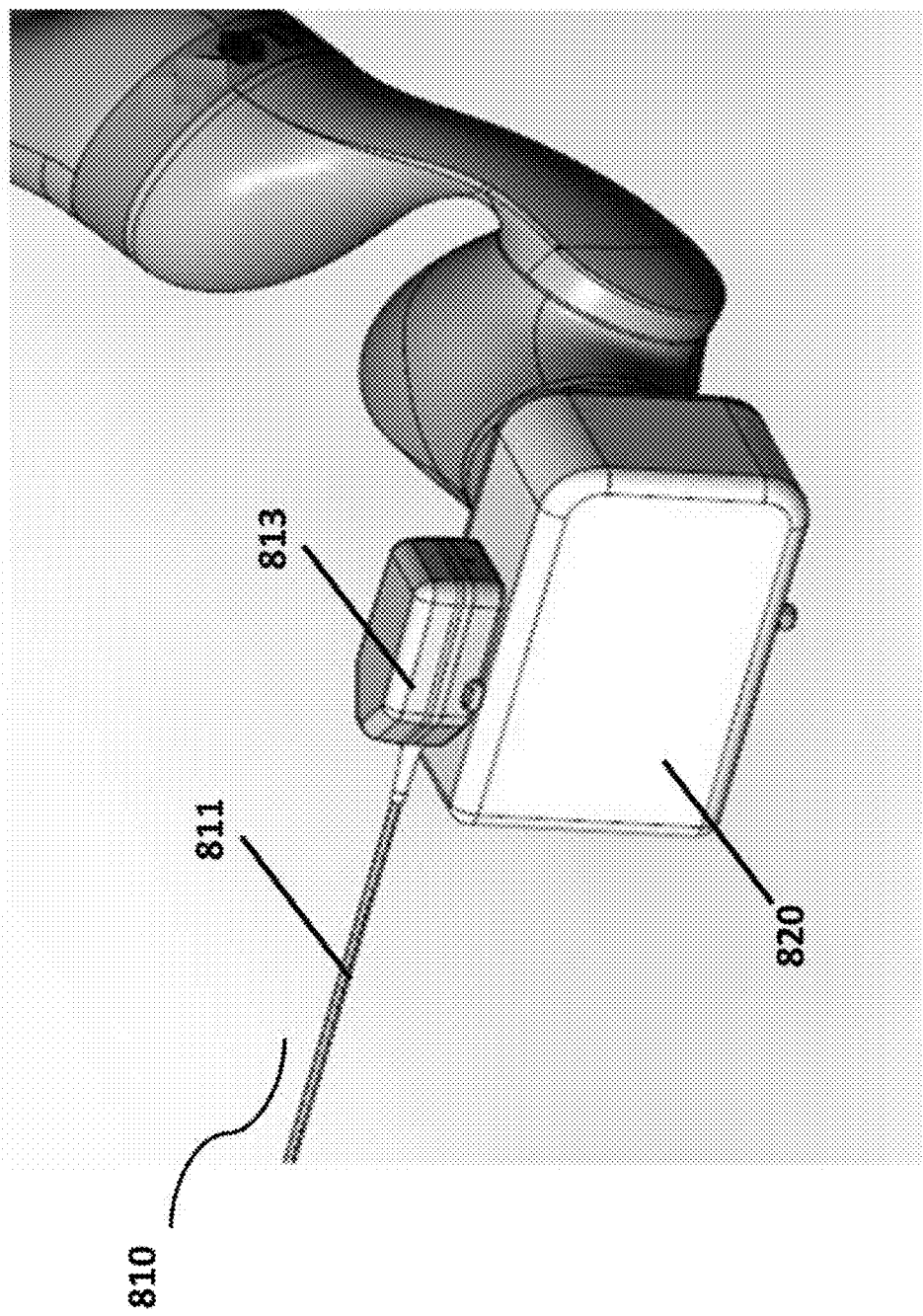
FIG. 8 shows an example of a robotic bronchoscope, in accordance with some embodiments of the invention.

FIG. 8 shows an example of a robotic bronchoscope system supported by a robotic support system. In some cases, the handle portion may be in electrical communication with the instrument driving mechanism (e.g., instrument driving mechanism 820) via an electrical interface (e.g., printed circuit board) so that image/video data and/or sensor data can be received by the communication module of the instrument driving mechanism and may be transmitted to other external devices/systems. In some cases, the electrical interface may establish electrical communication without cables or wires. For example, the interface may comprise pins soldered onto an electronics board such as a printed circuit board (PCB). For instance, receptacle connector (e.g., the female connector) is provided on the instrument driving mechanism as the mating interface. This may beneficially allow the endoscope to be quickly plugged into the instrument driving mechanism or robotic support without utilizing extra cables. Such type of electrical interface may also serve as a mechanical interface such that when the handle portion is plugged into the instrument driving mechanism, both mechanical and electrical coupling is established. Alternatively or in addition to, the instrument driving mechanism may provide a mechanical interface only. The handle portion may be in electrical communication with a modular wireless communication device or any other user device (e.g., portable/hand-held device or controller) for transmitting sensor data and/or receiving control signals.

As shown in FIG. 8, a robotic bronchoscope 820 may comprise a handle portion 813 and a flexible elongate member 811. In some embodiments, the flexible elongate member 811 may comprise a shaft, steerable tip and a steerable section. The robotic bronchoscope 820 can be the same as the steerable catheter assembly as described in FIG. 1. The robotic bronchoscope may be a single-use robotic endoscope. In some cases, only the catheter may be disposable. In some cases, at least a portion of the catheter may be disposable. In some cases, the entire robotic bronchoscope may be released from the instrument driving mechanism and can be disposed of. The bronchoscope may contain varying levels of stiffness along its shaft, as to improve functional operation.

The robotic bronchoscope can be releasably coupled to an instrument driving mechanism 820. The instrument driving mechanism 820 may be mounted to the arm of the robotic support system or to any actuated support system as described elsewhere herein. The instrument driving mechanism may provide mechanical and electrical interface to the robotic bronchoscope 820. The mechanical interface may allow the robotic bronchoscope 820 to be releasably coupled to the instrument driving mechanism. For instance, the handle portion of the robotic bronchoscope can be attached to the instrument driving mechanism via quick install/release means, such as magnets and spring-loaded levels. In some cases, the robotic bronchoscope may be coupled or released from the instrument driving mechanism manually without using a tool.

In some cases, a separate instrument driving mechanism may be used to control the movement of the hybrid probe. For example, a proximal portion of the hybrid probe may be coupled to a second instrument driving mechanism to articulate the tip of the hybrid probe. Alternatively or additionally, a roll movement of the hybrid probe may be controlled by a controller that is operably coupled to the controller of the catheter. This may beneficially provide a robotic control of both the hybrid probe and the catheter thereby allowing for a coordinated control of the hybrid probe and catheter with minimal user input.

Figure 9:
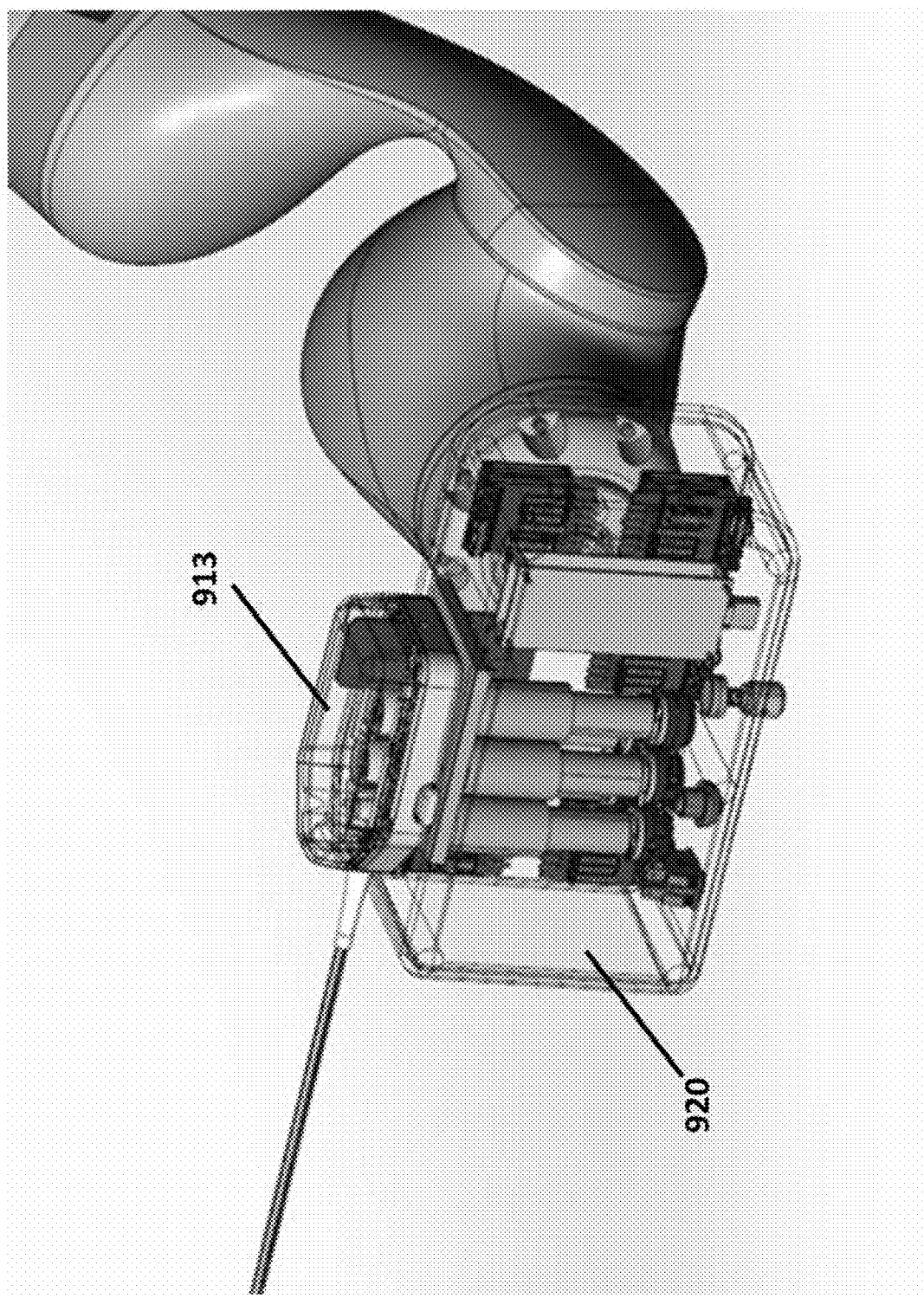
FIG. 9 shows an example of an instrument driving mechanism providing a mechanical and electrical interface to a handle portion of a robotic bronchoscope, in accordance with some embodiments of the invention.

FIG. 9 shows an example of an instrument driving mechanism 920 providing mechanical interface to the handle portion 913 of the robotic bronchoscope. As shown in the example, the instrument driving mechanism 920 may comprise a set of motors that are actuated to rotationally drive a set of pull wires of the catheter. The handle portion 913 of the catheter assembly may be mounted onto the instrument drive mechanism so that its pulley assemblies are driven by the set of motors. The number of pulleys may vary based on the pull wire configurations. In some cases, one, two, three, four, or more pull wires may be utilized for articulating the catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

In some case, the handle portion may be housing or comprise components configured to process image data, provide power, or establish communication with other external devices. In some cases, the communication may be wireless communication. For example, the wireless communications may include Wi-Fi, radio communications, Bluetooth, IR communications, or other types of direct communications. Such wireless communication capability may allow the robotic bronchoscope function in a plug-and-play fashion and can be conveniently disposed after single use. In some cases, the handle portion may comprise circuitry elements such as power sources for powering the electronics (e.g. camera and LED light source) disposed within the robotic bronchoscope or catheter.

The handle portion may be designed in conjunction with the catheter such that cables or fibers can be eliminated. For instance, the catheter portion may employ a design having working channel allowing instruments to pass through the robotic bronchoscope, a vision channel allowing a hybrid probe to pass through, as well as low cost electronics such as a chip-on-tip camera, illumination sources such as light emitting diode (LED) and EM sensors located at optimal locations in accordance with the mechanical structure of the catheter. This may allow for a simplified design of the handle portion. For instance, by using LEDs for illumination, the termination at the handle portion can be based on electrical soldering or wire crimping alone. For example, the handle portion may include a proximal board where the camera cable, LED cable, and EM sensor cable terminate while the proximal board connects to the interface of the handle portion and establishes the electrical connections to the instrument driving mechanism. As described above, the instrument driving mechanism is attached to the robot arm (robotic support system) and provides a mechanical and electrical interface to the handle portion. This may advantageously improve the assembly and implementation efficiency as well as simplify the manufacturing process and cost. In some cases, the handle portion along with the catheter may be disposed of after a single use.

Referring back to FIG. 1, in some cases, the distal tip of the bronchoscope may include positional sensors such as EM sensor 113 for tracking a location of the distal tip of the bronchoscope relative to a global reference frame or patient anatomy.

The catheter of the bronchoscope may include a lumen sized to receive the hybrid probe and a lumen or working channel 130 to receive an instrument. Various instruments can be inserted through the lumen such as biopsy needle, graspers, scissors, baskets, snares, curette, laser fibers, stitching tools, balloons, morcellators, various implant or stent delivery devices, and the like. In some cases, the EM sensor 113 tracked distal tip location may be registered to the ultrasound imaging (provided by the hybrid probe) such that the position of the distal tip of the catheter and/or the instrument carried in the working channel 130 relative to a lesion location identified by the ultrasound can be determined. In some cases, the movement of the instrument may be captured in the linear EBUS view 122.

The hybrid probe 120 may include at least a positional sensor such as EM sensor 123 and an ultrasound transducer 121. The transducer 121 may include an array of one or more transducers to perform real-time ultrasound imaging. In some cases, the transducer may include convex ultrasound transducer located at the tip of the probe and allows linear scanning parallel to the insertion direction of the bronchoscope in order to assess structures around the central airways (e.g., linear EBUS view 122). The linear EBUS view is parallel to the insertion direction of the bronchoscope. This can be performed by direct contact of the hybrid probe with the airway wall or via a distal balloon inflated with water.

The hybrid probe can be connected to an ultrasound scanner with a color Doppler system to better differentiate solid and vascular structures. In an example, the ultrasound transducer may include a linear curved array ultrasound transducer of 7.5 MHz located at the distal portion of the probe to provide imaging in B-mode and/or color Doppler mode. The ultrasound imaging system may provide an ultrasound view 122 by scanning a field of view certain degrees from the longitudinal axis or a degree forward oblique the camera view. As an example with no intention to be limiting, the ultrasound imaging system may provide a scanning range defined by a field of view in a range of 30° to 80°, a direction of view in a range of 25°-90° forward oblique and a depth of field in a range of 2-80 mm.

The hybrid probe 120 may include a positional sensor such as EM sensor 123. The EM sensor may be positioned at the distal portion of the hybrid probe for tracking a real-time location of the distal location of the probe relative to a global reference frame. In some cases, the EM sensor can be optional whereas the location of the distal tip of the hybrid probe may be obtained based on the EM sensor data provided by the EM sensor 113 located at the bronchoscope and a relative position of the hybrid probe with respect to the tip of the bronchoscope. The EM sensor 113 located at the distal tip of the catheter and the EM sensor 123 located at hybrid probe may be used to robotically control the location/motion of the hybrid probe and bronchoscope. For example, control command may be generated based on the positional information (e.g., EM sensor data captured by the EM sensor 113 and EM sensor 123) to coordinate the movement of the catheter 110 and the hybrid probe 120.

In some cases, the hybrid probe 120 may include an imaging device such as a camera 124. The camera 124 may be located at the tip of the hybrid probe to provide a forward video/camera view 125 that is parallel to the longitudinal axis of the probe. Alternatively, the camera 124 may be integrated into the distal tip 111 of the bronchoscope.

In some embodiments, the hybrid probe 120 may include an illumination device 126 located at the distal end of the probe. The illumination device may comprise one or more light sources positioned at the distal tip of the hybrid probe 120. The illumination device may be located at the distal end of the hybrid probe. Alternatively or additionally, the illumination device may be located at the distal end of the articulating bronchoscope 110. The light source may be a light-emitting diode (LED), an organic LED (OLED), a quantum dot, or any other suitable light source. In some cases, the light source may be a miniaturized LED for a compact design or Dual Tone Flash LED Lighting. In some cases, the illuminating device may fiber-based illumination, that can include single fibers or fiber bundles coupled to LEDs or lasers.

In some cases, each of the one or more LEDs may be connected to power wires which may run to the proximal handle of the hybrid probe. In some embodiments, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out.

The imaging device 124, the illumination device, EM sensor 123 and the ultrasound transducer may be integrated to the hybrid probe. For example, the distal portion of the hybrid probe may comprise suitable structures matching at least a dimension of the above electronics. In some cases, the distal tip of the hybrid probe may have a dimension so that the one or more electronic components can be embedded into the distal tip. For instance, the imaging device 124 may be embedded into a cavity at the distal tip of the hybrid probe. The cavity may be integrally formed with the distal portion of the hybrid probe and may have a dimension matching a length/width of the camera such that the camera may not move relative to the hybrid probe.

Figure 10:
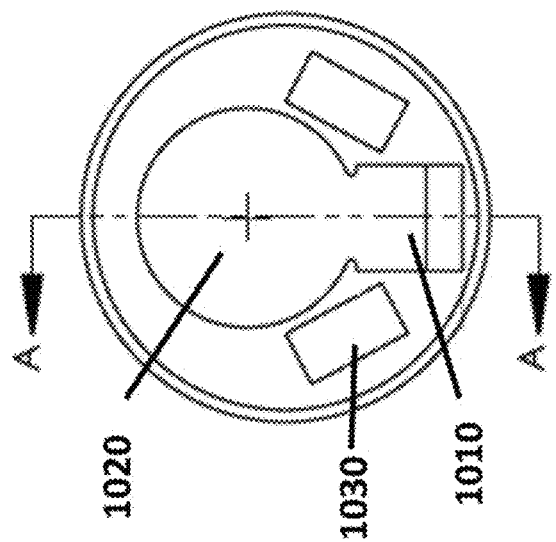
FIG. 10 shows an example of a distal portion of a hybrid probe with integrated imaging device and the illumination device.
Figure 10:
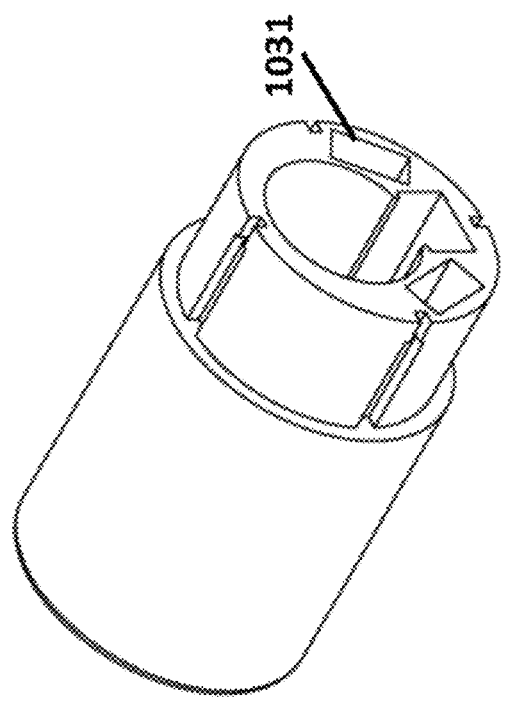

In some cases, the EM sensor 123 may be disposed at the distal portion of the hybrid probe and may be placed adjacent to or behind the illumination light sources (e.g., LEDs) in a stereoscopic arrangement. FIG. 10 shows an example of the distal portion of the hybrid probe with integrated imaging device and the illumination device. It should be noted that the distal tip design of the hybrid probe is also applicable to the distal tip of the catheter with integrated vision as described in FIG. 4. A camera may be located at the distal portion. The distal tip may have a structure to receive the camera, illumination device and/or the location sensor. For example, the camera may be embedded into a cavity 1010 at the distal tip of the catheter. The cavity 1010 may be integrally formed with the distal portion of the cavity and may have a dimension matching a length/width of the camera such that the camera may not move relative to the catheter. In some cases, the distal portion may comprise a structure 1030 having a dimension matching a dimension of the miniaturized LED light source. As shown in the illustrated example, two cavities 1030 may be integrally formed with the distal portion to receive two LED light sources. Any number of light sources may be included. The internal structure of the distal portion may be designed to fit any number of light sources.

Figure 4:
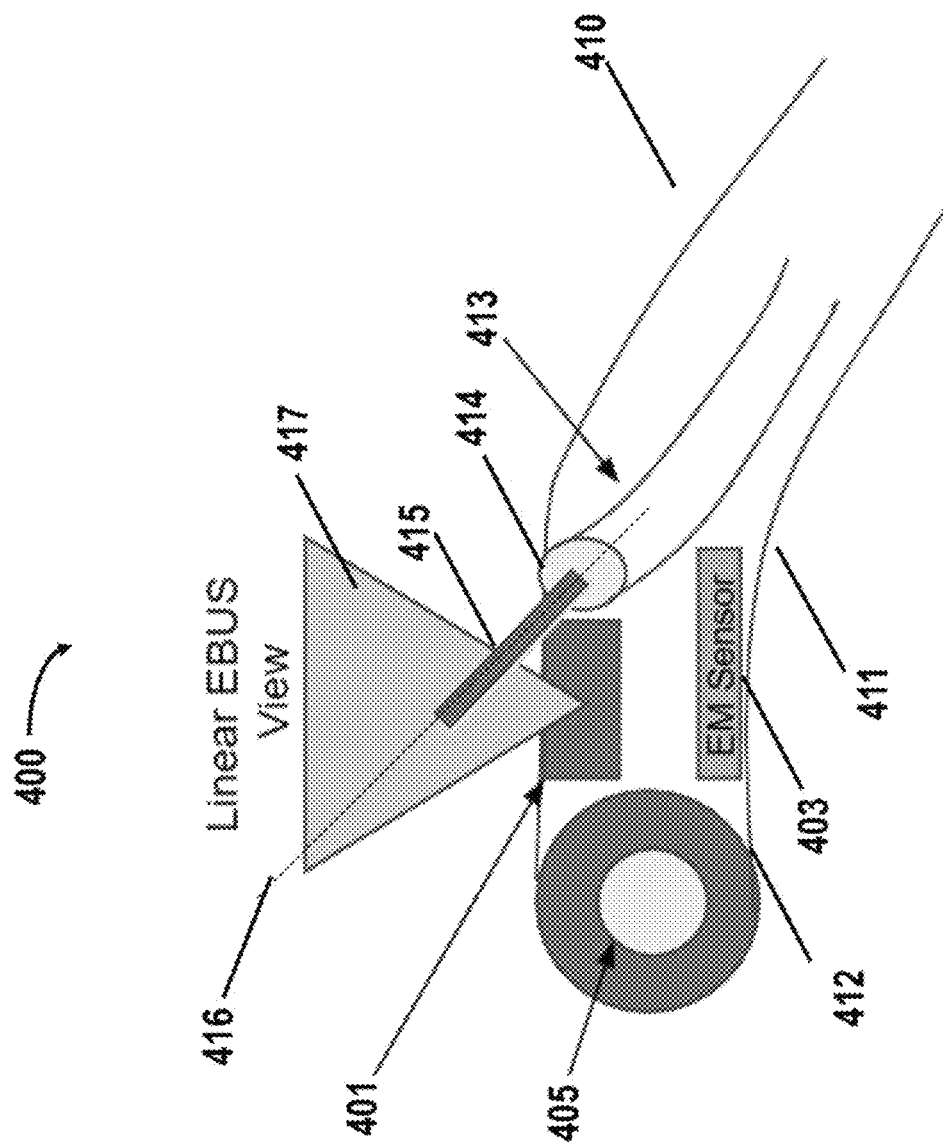
FIG. 4 shows an example of an endoscope with integrated hybrid vision, in accordance with some embodiments of the present disclosure.

In some cases, each of the LEDs may be connected to power wires which may run to the proximal end of the hybrid probe or bronchoscope (e.g., integrated vision embodiments described in FIG. 4). In some embodiment, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover 1031 may be placed at the forwarding end face of the distal tip providing precise positioning of the LEDs as well as sufficient room for the glue. The cover 1031 may be composed of transparent material matching the refractive index of the glue so that the illumination light may not be obstructed.

Electromagnetic coils located on the distal end may be used with an electromagnetic tracking system to detect the position and orientation of the distal end of the hybrid probe while it is disposed within an anatomical system. In some embodiments, the coils may be angled to provide sensitivity to electromagnetic fields along different axes, the ability to measure a full 6 degrees of freedom: three positional and three angular. During navigation such as when the hybrid probe withdraws inside the catheter, the EM field generator positioned next to, under, or above, a patient torso may locate the EM sensors thereby tracking the location of the catheter tip in real-time. During the procedure such as when the hybrid probe is extended out distally of the catheter, the EM sensor may track the location of the tip of the hybrid probe in real-time.

Figure 11:
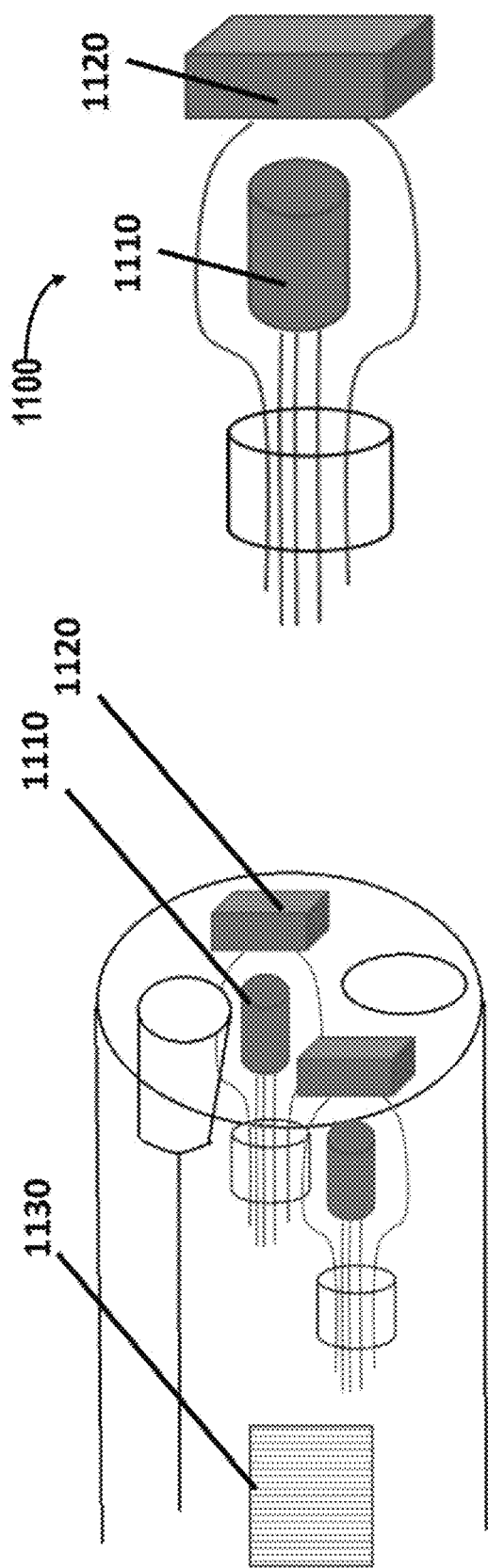
FIG. 11 shows an example of a compact configuration of the electronic elements located at the distal portion.

Referring back to FIG. 1, the provided hybrid probe may have a compact configuration of the electronic elements disposed at the distal portion. For example, one or more electronic components may be bundled to provide a compact design. FIG. 11 shows an example of a compact configuration of the electronic elements located at the distal portion. In some cases, the illumination light source 1120 and one or more position sensors 1110 may be combined into a bundle. In some cases, the cable connected to the ultrasound transducer 1130 may also be bundled with the cable of the other electronics to further reduce the dimension of the hybrid probe.

Referring back to FIG. 1, the power to the camera 124 may be provided by a wired cable. In some cases, the cable wire may be in wire bundle providing power to the camera as well as the illumination elements or other circuitry at the distal tip of the hybrid probe. The camera and/or light source may be supplied with power from a power source disposed in the handle portion of the hybrid probe via wires, copper wires, or via any other suitable means running through the length of the hybrid probe. In some cases, real-time images or video of the tissue or organ may be transmitted to external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the hybrid probe to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

As described above, the hybrid probe is movable relative to the bronchoscope. The hybrid probe may have a translational movement along the longitudinal axis of the lumen and a rotational movement relative to the bronchoscope. For example, the hybrid probe may be extendible relative to the distal tip of the bronchoscope. For example, the hybrid probe may be slidable along the lumen of the catheter. The tip of the hybrid probe may extend out along the longitudinal axis of the distal tip of the bronchoscope when the hybrid vision is needed. Alternatively or additionally, the hybrid probe may be articulated independent of the bronchoscope. For example, the hybrid probe may have a bending section that can be articulated independent of the motion of the bronchoscope.

As described above, the imaging device located at the hybrid probe may provide a forward-looking view aligned with the forward direction of the hybrid probe. Providing the imaging device on the distal tip of the hybrid probe instead of the catheter may beneficially allow for a clear near field view of the tissue or organs without being blocked by the operation of the hybrid probe or tools (e.g., needle). Additionally, providing the imaging device on the hybrid probe allows for an additional degree of freedom for the camera view to decouple the camera field of view from the workspace of the tools. The camera view provided by the hybrid probe can be controlled with improved flexibility (e.g., attitude or orientation of the imaging device may be controlled by controlling the articulation of the hybrid probe relative to the catheter) to better coordinate with operations of the tools.

In some cases, an additional imaging device may be provided at the distal tip of the catheter 111. This beneficially allows for simultaneous different camera views provided by the imaging devices located at the hybrid probe and the catheter. For instance, when the hybrid probe is articulated with respect to the catheter, the camera view of the imaging device located at the hybrid probe may be different from the camera view of the imaging device located at the catheter.

In some cases, the catheter/bronchoscope and the hybrid probe may be robotically controlled to coordinate the camera views of the imaging devices and operation of the tools. For example, the catheter may be advanced toward the target site under a robotic control of a robotic bronchoscope system. Once it reaches the target site, the distal tip of the catheter may be locked to provide a forward looking camera view while the hybrid probe may be robotically controlled (e.g., extend, retract, articulate, rotate/roll relative to the catheter) to provide a desired ultrasound view of the lesion site and/or camera view of the needle. In some cases, the hybrid probe may automatically adjust the view based on an operation of the tools (e.g., needle).

Figure 2:
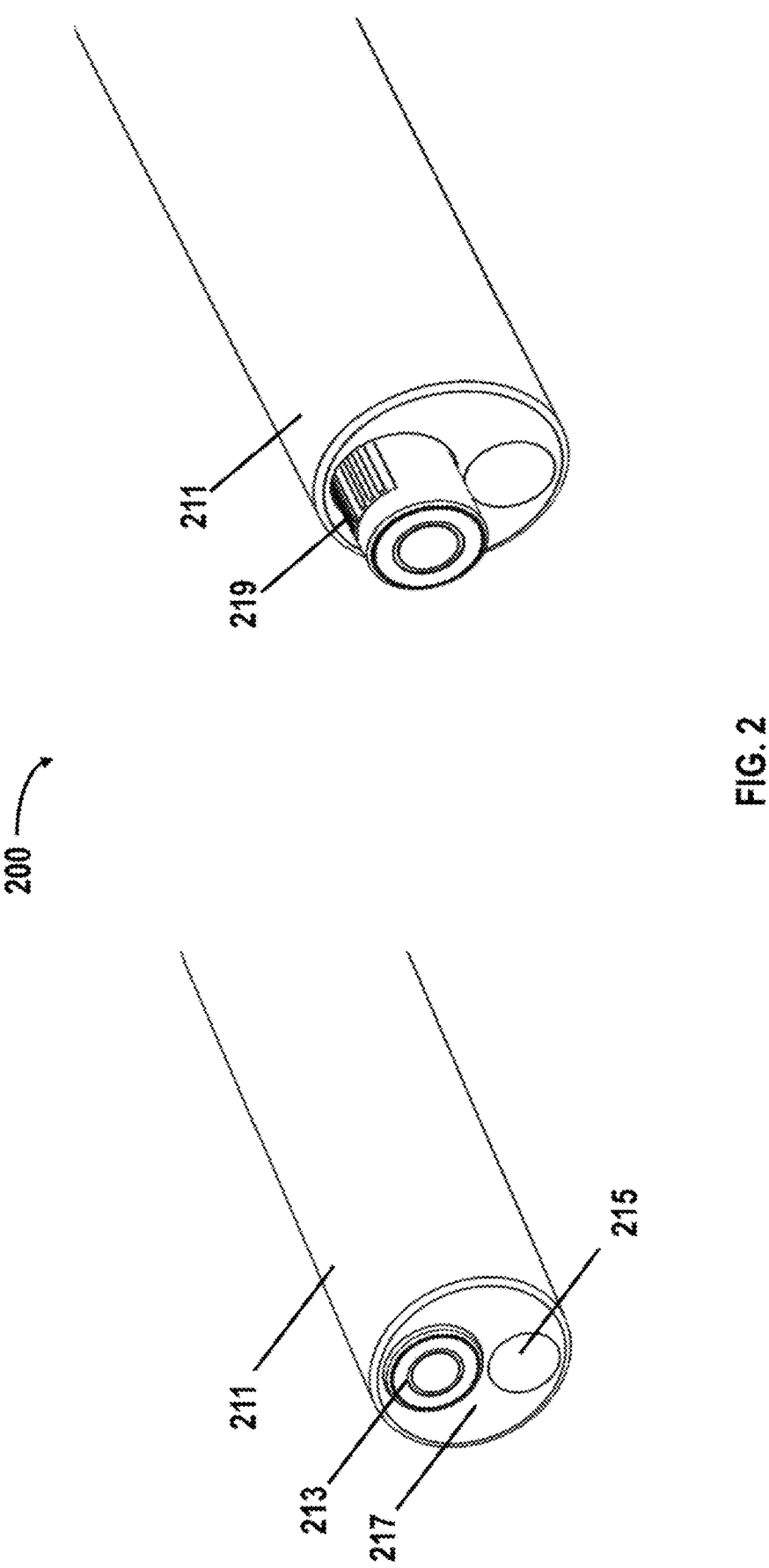
FIG. 2 shows examples of a hybrid probe that can be extended distally over the distal tip of the bronchoscope, in accordance with some embodiments of the present disclosure.

FIG. 2 shows examples 200 of a hybrid probe 213 that can be extended distally over the distal tip 211 of the bronchoscope. The bronchoscope can be the same as the bronchoscope as described in FIG. 1. For example, the bronchoscope may include at least a working channel 215 for receiving instrument and an EM sensor located at the distal tip. In some cases, during navigation to the target site where only direct vision (e.g., camera view) is needed, the hybrid probe may be flush against a distal end surface 217 of the catheter. In some cases, when an ultrasound image is desired, the hybrid probe may be extended past the catheter tip to expose the ultrasound transducer 219. The hybrid probe and the bronchoscope may comprise reversible interlock features which lock the position of the hybrid probe relative to the bronchoscope to prevent axial movement and/or rotational movement. In some cases, when the hybrid probe is operating to provide ultrasound imaging, it may be rotatable relative to the bronchoscope to locate a lesion site. For example, when the hybrid probe is extended to a desired length and/or rotated to a desired angle, the interlock feature may lock the location/orientation of the hybrid probe relative to the bronchoscope.

Figure 3:
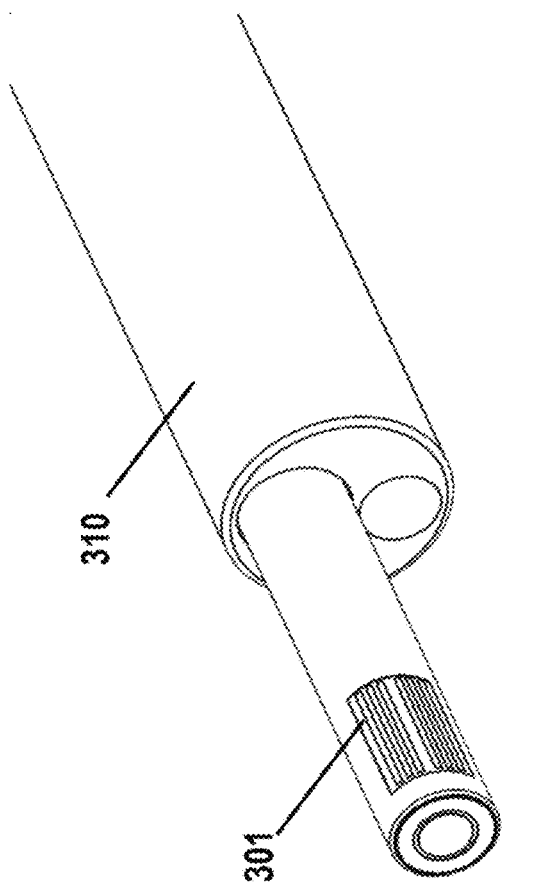
FIG. 3 shows examples of a hybrid probe rotated relative to a distal portion of a catheter, in accordance with some embodiments of the present disclosure.
Figure 3:
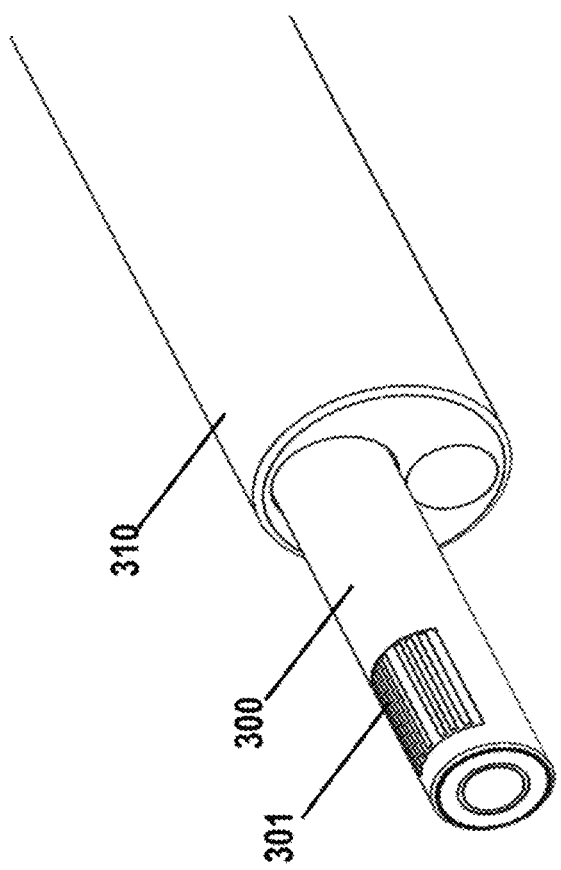

FIG. 3 shows examples of the hybrid probe 300 rotated relative to the distal portion 310 of the catheter. The ultrasound transducer 301 can be rotated to any desired location to provide imaging surround the tip of the probe. As shown in the example, the hybrid probe 300 is extended over the tip of the catheter to a desired extent and the ultrasound transducer 301 can be rotated to different angular locations for imaging. In some cases, once the hybrid probe is positioned into the desired angular location and/or length location, the interlock feature may lock the location of the hybrid probe relative to the bronchoscope.

The hybrid probe may be rotated independent of the catheter, such that any point surrounding the distal portion of the hybrid probe may be visualized by rotating the hybrid probe. The rotational movement of the hybrid probe may be controlled robotically or manually. The rotation maneuver may allow a user to reposition the linear ultrasound field of view throughout the entire circumference of the airways. For example, a lesion location may be identified with aid of the EBUS and by rotating the hybrid probe, once the location of the lesion is identified, the catheter may be repositioned accordingly (e.g., insertion or rotational movement) such that a biopsy instrument can be introduced and advanced out of the working channel and directly into the lesion location.

In some embodiments, the ultrasound transducer and the camera may be integrated into the bronchoscope as a single device. FIG. 4 shows an example of an endoscope 400 with integrated hybrid vision. As illustrated in the example, the distal tip of the endoscope may include an integrated forward-looking camera 405 and illumination source for direct visualization, along with an integrated linear ultrasound probe 401 facing the lateral direction. One or more positional sensors such as EM sensor 403 may also be integrated into the distal tip.

The imaging device, the illumination device, EM sensor and the ultrasound transducer may be integrated to the catheter. For example, the distal portion of the catheter may comprise suitable structures matching at least a dimension of the above electronics. In some cases, the distal tip of the catheter may have a dimension so that the one or more electronic components can be integrated to the catheter. For example, the outer diameter of the distal tip may be around 4 to 4.4 millimeters (mm), and the diameter of the working channel may be around 2 mm such that one or more electronic components can be embedded into the distal tip. However, it should be noted that based on different applications, the outer diameter can be in any range smaller than 4 mm or greater than 4.4 mm, and the diameter of the working channel can be in any range according to the tool dimensional or specific application.

The EM sensor, camera and ultrasound transducer can be the same as those as described elsewhere herein. For example, the camera may be a chip-on-tip camera and the illumination source may be a light-emitting diode (LED), an organic LED (OLED), a quantum dot, or any other suitable light source. In some cases, the light source may be miniaturized LED for a compact design or Dual Tone Flash LED Lighting. In some cases, the abovementioned electronics may be embedded into the tip of the catheter.

The distal bronchoscope may include a working channel 413 with a side exist/port 414. In some cases, the side exit 414 may be located at the articulating section 411 of the catheter. The catheter may comprise a shaft 410, an articulation (bending) section 411 and a steerable distal portion 412, where articulation section (bending section) 411 is connecting the steerable distal portion to the shaft 410. For example, the bending section 411 may be connected to the distal tip portion at a first end, and connected to a shaft portion at a second end, where the bending section is articulated by one or more pull wires. In some cases, the bending section may be fabricated separately as a modular component and assembled to the shaft. In some cases, the bending section may further incorporate minimalist features thereby reducing cost and increasing reliability. For example, the bending section may incorporate a cut pattern that beneficially allows for a greater degree of tube deflection to achieve a desired tip displacement relative to the shaft. In some cases, the bending section may be composed of stainless steel ribbon. The bending section may be formed of other suitable structures or materials to achieve predetermined bending stiffness while maintaining desired axial and torsional stiffness with low articulation force. For example, the bending section may comprise braid structures for torsional stability.

The side port 414 is located at the bending section 411. The distal end of an instrument is extendable along a path from a position within the elongate flexible shaft and through the side exit to an extended position outside the catheter at an angle θ relative to the longitudinal axis of the tip of the catheter. This may allow the instrument to be extended out of the side port 414 and fall within the EBUS view 417 (to be captured by the ultrasound) even without articulating the instrument.

The lumen of the working channel may have a port located at the bending section and the lumen have allow the instrument to extend out of the port along a trajectory that intersects the EBUS view. For example, as shown in FIG. 4, the working channel exit trajectory 416 intersects with the field of view 417 of the linear endobronchial ultrasound (EBUS) or the image captured by the ultrasound. A biopsy device 415 (e.g., forceps, needle, brush) may be extendable along a path from a position within the outer wall through a side exit/port to a position outside the outer wall at an angle of at least 30 degrees with respect to the longitudinal axis. The path of the biopsy device 415 may pass/intersect the EBUS field of view (e.g., ultrasound image) such that at least a tip portion of the instrument can be viewed in the ultrasound image. In some cases, the path of biopsy device can be calibrated to the location of an electromagnetic localization (EM) sensor 403 positioned at the distal end portion of the elongate flexible shaft 410 and displayed by a surgical instrument navigation system.

A steerable catheter may be rotated, such that any point surrounding the distal end of the catheter may be visualized by rotating the catheter. The rotational movement of the catheter may be robotically controlled. The rotation maneuver may allow a user to reposition the linear ultrasound field of view throughout the entire circumference of the airways. For example, a lesion location may be identified with aid of the EBUS and by rotating the catheter, once the location of the lesion is identified, the biopsy instrument can be introduced and advanced out of the working channel and directly into the lesion location.

In some embodiments, the hybrid vision assembly may comprise a bronchoscope with integrated direct vision and location sensing, and a hybrid probe with a balloon. The distal end of the bronchoscope may include an integrated forward-looking camera and illumination for direct visualization, along with an integrated EM sensor (e.g., at least 3 degrees of freedom) to generate 3D localization information.

Figure 5:
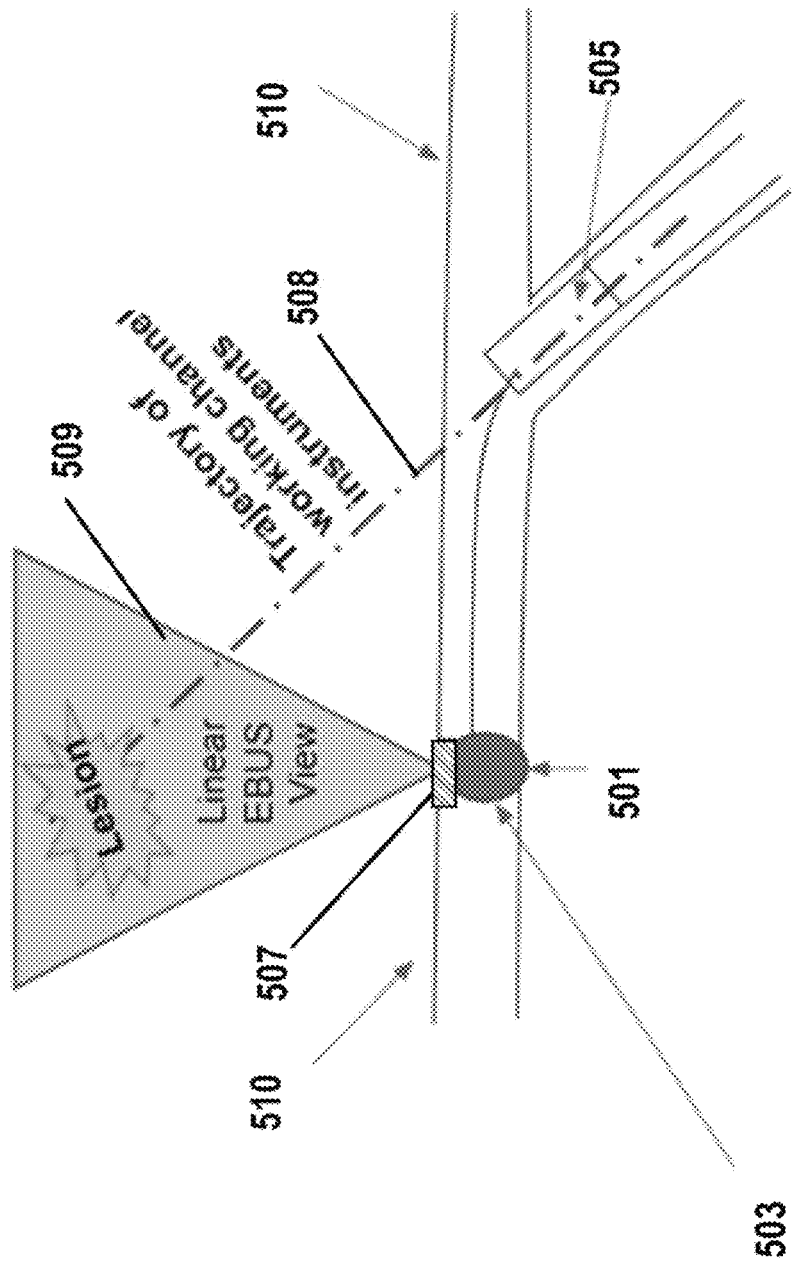
FIG. 5 shows an example of a hybrid probe with an inflatable tip, in accordance with some embodiments of the present disclosure.

In some cases, the hybrid probe may include at least an ultrasound transducer and an EM sensor located at the distal portion of the hybrid probe and are covered by one or more balloons. In some cases, the hybrid probe may include a guidewire having an expandable outside diameter feature at the tip where the EBUS transducer and EM sensor located. FIG. 5 shows an example of a hybrid probe with an inflatable tip 503. As shown in FIG. 5, the working channel exit trajectory 508 intersects with the linear EBUS view 509 of the linear endobronchial ultrasound (EBUS) or the ultrasound image. The hybrid probe may be inserted through a working channel of the catheter/bronchoscope 505 and extended over the catheter to assist in navigation of the air passages 510 in the lung. In some cases, the tip of the hybrid probe may be extended past the tip of the catheter into the desired airway 510 and the catheter may then slide over the guidewire/probe to reach the desired location. The inflatable tip can be implemented using various suitable methods such as an inflatable balloon. The balloon 503 may be positioned at or close to the distal end of the probe and may cover the linear EBUS transducer 507 and the EM sensor 501. The balloon may be connected through the working channel to a balloon inflation source or pump for inflation or deflation of the balloon.

In some cases, the balloon may also create a seal across one of passageways at a seal point, prior to collapsing passageways distal to the seal point. By injecting air, saline, and/or some other gas or fluid, the one or more balloons may be expanded and/or collapsed to create a temporary closure in the passageway. In some examples, a shape of the balloon upon expanding is malleable, allowing the balloon to conform to a shape of the passageway, to expand around the one or more sensors and the tip of the hybrid probe.

The EM sensor and the ultrasound transducer can be the same as those as described elsewhere herein. For example, the EM sensor located at the tip of the catheter 505 and the EM sensor covered by the balloon may be a 6 DOF EM sensor.

Figure 6:
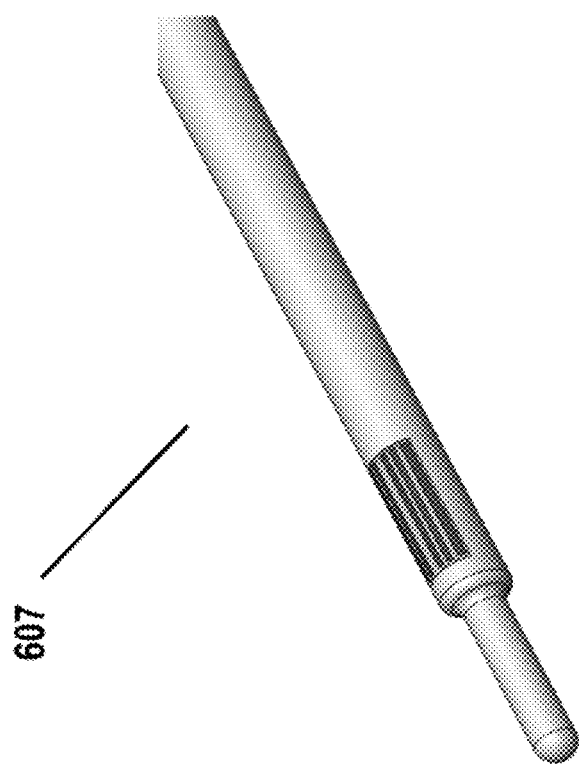
FIG. 6 shows examples of a hybrid probe with a balloon tip, in accordance with some embodiments of the present disclosure.
Figure 6:
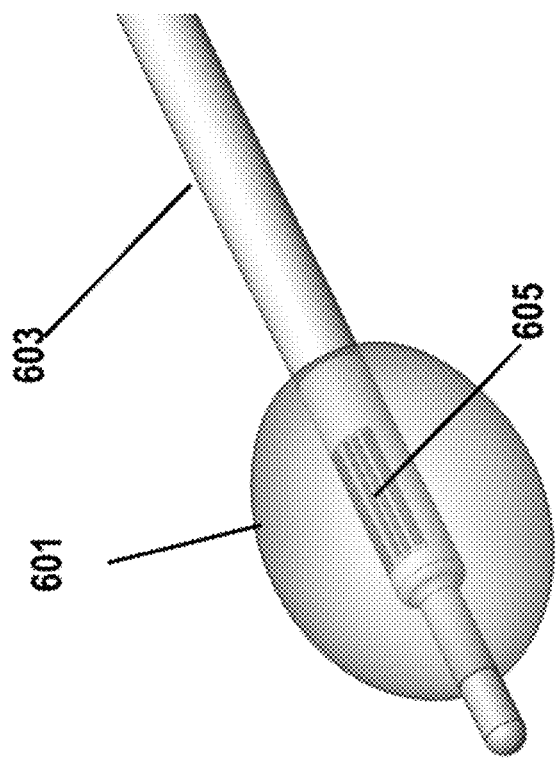

FIG. 6 shows examples of the hybrid probe 603 with a balloon tip. For example, the hybrid probe 603 may provide an ultrasound view of a lesion site, along with 3D localization information from the EM sensor. The balloon 601 may cover the EM sensor and the ultrasound transducer 605. A hybrid probe 607 with collapsed balloon is shown. In some cases, the EM sensor information can be registered and correlated with the ultrasound image. The hybrid probe may be removably coupled to the catheter. The hybrid probe may be movable relative to the catheter such as can be inserted and retracted along a longitudinal axis of the catheter and rotated in order to capture various ultrasonic views and EM data points. Once a lesion site is identified and the lesion's 3D location is determined, a physician may manipulate the position of the bronchoscope in order to align the trajectory of the biopsy tool with the location of the lesion. The position or the trajectory of the biopsy tool may be determined based at least in part on the location date provided by the EM sensor located at the distal tip of the catheter and a known model of the catheter and/or the instrument.

The catheter, the bronchoscope, and/or the hybrid probe can be robotically controlled. For example, the catheter may be advanced toward the target site under a robotic control of a robotic bronchoscope system. The catheter may be steered or advanced towards the target site in a manual manner, an autonomous manner, or a semi-autonomous manner. In another example, the movement of the hybrid probe may be automatically controlled such that the insertion, retraction, rotational movement for taking ultrasound images may be controlled automatically. Alternatively, the bronchoscope, and/or the hybrid probe can be controlled via a hand-held device.

User Interface

Figure 7:
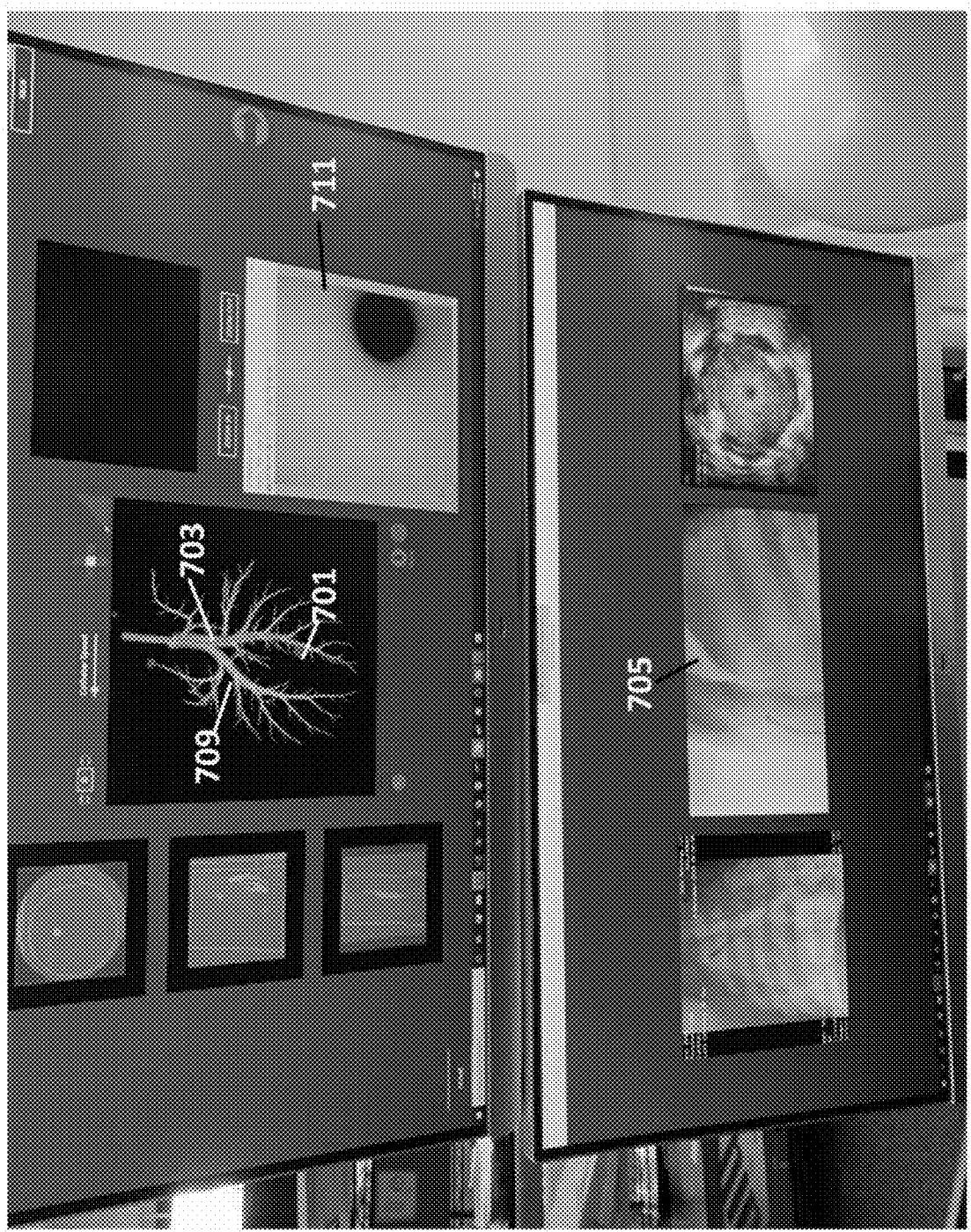
FIG. 7 shows an example of a user interfacing displaying endobronchial ultrasound (EBUS) view for real-time accurate lesion location tracking, a direct video/camera view and a virtual airway model based on the pre-operative image.

In some embodiments, real-time imaging of a target site (e.g., comprising lesion) provided by the multimodal sensing system may be displayed on a user interface. FIG. 7 shows an example of a user interfacing displaying EBUS view for real-time accurate lesion location tracking, a direct video/camera view and a virtual airway model based on the pre-operative image (e.g., pre-op CT image).

In some cases, real-time lesion location may be identified from the ultrasound view. The lesion location may be registered with the coordinate frame of the bronchoscopy system using the EM sensor data. In some embodiments, a location of lesion may be segmented in the image data captured by the linear EBUS probe with aid of a signal processing unit. In some cases, one or more processors of the signal processing unit may be configured to overlay treatment locations (e.g., lesion) on the real-time ultrasound image/video. In some cases, both the segmented lesion images and an optimum path for navigation of the elongate member to reach the lesion may be overlaid onto the real time ultrasound images. This may allow operators or users to visualize the accurate location of the lesion as well as a planned path of the bronchoscope movement.

In some embodiments, the bronchoscope system may include a navigation and localization subsystem configured to construct a virtual airway model based on the pre-operative image (e.g., pre-op CT image). The navigation and localization subsystem may be configured to identify an approximate segmented lesion location in the 3D rendered airway model and based on the location of the lesion, the navigation and localization subsystem may generate an optimal path from the main bronchi to the lesions with a recommended approaching angle towards the lesion for performing surgical procedures (e.g., biopsy). For example, a processing unit may be configured to generate an augmented layer comprising augmented information such as the location of the treatment location or the lesion. In some cases, the augmented layer may also comprise graphical marker indicating a path to this target site. The augmented layer may be a substantially transparent image layer comprising one or more graphical elements (e.g., box, arrow, etc). The augmented layer may be superposed onto the optical view of the optical images or video stream captured by the fluoroscopy (tomosynthesis) imaging system, and/or displayed on the display device. The transparency of the augmented layer allows the optical image to be viewed by a user with graphical elements overlay on top of. In some cases, both the segmented lesion images and an optimum path for navigation of the elongate member to reach the lesion may be overlaid onto the virtual airway model or pre-operative images. This may allow operators or users to visualize the approximate location of the lesion as well as a planned path of the bronchoscope movement. In some cases, the segmented and reconstructed images (e.g. CT images as described elsewhere) provided prior to the operation of the systems described herein may be overlaid on the real time images.

At a registration step before driving the bronchoscope to the target site, the system may align the rendered virtual view of the airways to the patient airways. Image registration may consist of a single registration step or a combination of a single registration step and real-time sensory updates to registration information. Once registered, all airways may be aligned to the pre-operative rendered airways. During robotic bronchoscope driving towards the target site, the location of the bronchoscope inside the airways may be tracked and displayed. In some cases, location of the bronchoscope with respect to the airways may be tracked using positioning sensors. Other types of sensors (e.g. camera) can also be used instead of or in conjunction with the positioning sensors using sensor fusion techniques. Positioning sensors such as electromagnetic (EM) sensors may be embedded at the distal tip of the catheter and an EM field generator may be positioned next to the patient torso during procedure. The EM field generator may locate the EM sensor position in 3D space or may locate the EM sensor position and orientation in 5D or 6D space. This may provide a visual guide to an operator when driving the bronchoscope towards the target site.

During operation, the lesion location may be updated and tracked in real-time based on the ultrasonic view. In some cases, a location of the lesion may be marked on the ultrasound view and the distal tip of the bronchoscope may be articulated, rotated or moved to align the trajectory of the instrument with the lesion location.

In some embodiments, the processor may use the real-time location of one or more of the lesion, bronchoscope, hybrid probe, and the instrument to calculate one or more possible geometries/configurations as illustrated in FIG. 4 and FIG. 5. For example, the system may calculate the appropriate motion of the hybrid probe in order to establish the desired configuration (e.g., the trajectory, angle of the instrument, location of the EBUS view in FIG. 5) so that the instrument can access the lesion while under direct ultrasound imaging. Further, in some embodiments the system may partially or fully control the motion of the hybrid probe, bronchoscope, and instrument in order to establish the optimal geometry/configuration. For example, once the system knows and can track the location of all these elements, it may generate a plan to be executed by the robotic system to move the instrument, hybrid probe and bronchoscope into a desired configuration with respect to the lesion site. In some cases, guidance may be displayed to the user to manipulate one or more of the instruments, hybrid probe and bronchoscope. For instance, a user may be provided with guidance such as "stop the bronchoscope here", "move the hybrid probe to this location", "insert instrument now" and the like to reach the desired configuration. In some cases, the configuration may be reach in a semi-autonomous fashion. For example, a user may be permitted to activate/trigger a motion or stop a motion while the robotic system automatically controls the motion of the hybrid probe, instrument and/or bronchoscope (e.g. a user may hold activation trigger and the robotic system moves hybrid probe, instrument and/or bronchoscope when the trigger is being held). In some cases, the robotic system may stabilize the desired geometry/configuration by automatically tracking a breathing motion of a patient (e.g., breathing motion compensation).

FIG. 7 shows an example of a user interface for visualizing a real-time ultrasound image 705, virtual airway model 709 with EM tracked catheter tip location 701, and a direct camera view 711. In some cases, the virtual airway 709 is overlaid with an optimal path 703, location of the tip of the catheter 701, and an approximate location of a solitary pulmonary nodule (revealed by CT scan). In this example, the location of the tip of the catheter is displayed in real-time relative to the virtual airway model 709 thereby providing visual guidance. As shown in the example of FIG. 7, during robotic bronchoscope driving, the optimal path 703 may be displayed and overlaid onto the virtual airway model. The virtual airway model may be constructed based on the real-time fluoroscopic image/video (and location data of the imaging system). Users may also be presented with the camera view or image/video 711 captured by the bronchoscope and an ultrasound view 705 showing an accurate lesion location in real-time.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A hybrid vision device comprising:
an articulatable elongate member comprising a proximal end and a distal end, wherein a first positional sensor is located at the distal end of the articulatable elongate member, wherein the articulatable elongate member comprises a first lumen receiving a multimodal sensing probe and a second lumen receiving an instrument; and
the multimodal sensing probe removably coupled to the articulatable elongate member through the first lumen and extendable over a port of the first lumen at the distal end of the articulatable elongate member, wherein the multimodal sensing probe comprises an ultrasound transducer and a camera located at a distal portion of the multimodal sensing probe, and wherein the camera is configured to provide a camera view and the ultrasound transducer is configured to provide a side view oblique to the camera review thereby capturing a movement of the instrument when the instrument is extended over a port of the second lumen, wherein the multimodal sensing probe further comprises an interlock feature configured to lock a position of the multimodal sensing probe relative to the articulatable elongate member upon the multimodal sensing probe extended over the port of the first lumen at the distal end of the articulatable elongate member at a desired angular location or length location thereby preventing an axial movement or a rotational movement between the multimodal sensing probe and the articulatable elongate member.

2. The hybrid vision device of claim 1, wherein the multimodal sensing probe is rotatable relative to the articulatable elongate member.

3. The hybrid vision device of claim 1, wherein the multimodal sensing probe is articulatable relative to the articulatable elongate member.

4. The hybrid vision device of claim 1, wherein the articulatable elongate member further comprises an imaging device located at the distal end of the articulatable elongate member.

5. The hybrid vision device of claim 1, wherein the multimodal sensing probe comprises an inflatable tip.

6. The hybrid vision device of claim 1, wherein the proximal end of the articulatable elongate member is releasably coupled to a robotic support system via an instrument driving mechanism.

7. The hybrid vision device of claim 1, wherein the multimodal sensing probe further comprises a second positional sensor located at the distal portion of the multimodal sensing probe to track a location of the distal portion of the multimodal sensing probe.

8. The hybrid vision device of claim 7, wherein the second positional sensor, the camera and an illuminating device are embedded into the distal portion of the multimodal sensing probe.

9. The hybrid vision device of claim 7, wherein the articulatable elongate member and the multimodal sensing probe are robotically controlled based at least in part on the sensor data captured by the first positional sensor and the second positional sensor.

10. The hybrid vision device of claim 1, wherein the ultrasound transducer is an array of linear endobronchial ultrasound (EBUS) transducers.

11. The hybrid vision device of claim 10, wherein the side view is parallel to an insertion direction of the hybrid vision device.

12. The hybrid vision device of claim 10, wherein the linear EBUS transducer comprises a linear curved array ultrasound transducer of about 7.5 MHz.

13. The hybrid vision device of claim 10, wherein the linear EBUS transducer is configured to provide imaging in B-mode or color Doppler mode.

14. The hybrid vision device of claim 10, wherein the side view provided by the linear EBUS transducer is not a radial 360° view.

15. The hybrid vision device of claim 10, wherein a direction of the side view in a range of 25°-90° forward oblique to the camera view.

16. The hybrid vision device of claim 15, wherein the port of the second lumen is located at a bending section of the articulatable elongate member allowing the instrument to extend out the port along a trajectory that intersects the side view.

* * * * *